(12) United States Patent
Tsakonas

(10) Patent No.: US 7,922,770 B2
(45) Date of Patent: Apr. 12, 2011

(54) TOTAL KNEE ARTHROPLASTY ENDOPROSTHESIS WITH THIRD CONDYLE AND ROTATING POLYETHYLENE INSERT

(76) Inventor: Athanasios Tsakonas, Thessalonikl (GR)

(*) Notice: Subject to any disclaimer, the term of this patent is extended or adjusted under 35 U.S.C. 154(b) by 4 days.

(21) Appl. No.: 12/065,792

(22) PCT Filed: Mar. 16, 2007

(86) PCT No.: PCT/GR2007/000018
§ 371 (c)(1),
(2), (4) Date: Mar. 5, 2008

(87) PCT Pub. No.: WO2007/116232
PCT Pub. Date: Oct. 18, 2007

(65) Prior Publication Data
US 2009/0036992 A1      Feb. 5, 2009

(30) Foreign Application Priority Data
Apr. 7, 2006   (GR) .............................. 20060100216

(51) Int. Cl.
*A61F 2/38*   (2006.01)
(52) U.S. Cl. ................... 623/20.27; 623/20.31
(58) Field of Classification Search .... 623/20.14–20.16, 623/20.19, 20.21, 20.24, 20.27–20.29, 20.23, 623/20.31–20.35, 20.26
See application file for complete search history.

(56) References Cited

U.S. PATENT DOCUMENTS

| | | | | |
|---|---|---|---|---|
| 5,413,604 A | * | 5/1995 | Hodge | 623/20.28 |
| 5,824,105 A | * | 10/1998 | Ries et al. | 623/20.31 |
| 5,871,543 A | * | 2/1999 | Hofmann | 623/20.32 |
| 6,203,576 B1 | * | 3/2001 | Afriat et al. | 623/20.27 |
| 6,413,279 B1 | * | 7/2002 | Metzger et al. | 623/20.29 |
| 7,465,320 B1 | * | 12/2008 | Kito et al. | 623/20.27 |
| 2004/0243244 A1 | * | 12/2004 | Otto et al. | 623/20.27 |

FOREIGN PATENT DOCUMENTS

DE      30 39 992 A1      5/1981

(Continued)

OTHER PUBLICATIONS

H. S. Han et al, "High incidence of loosening of the femoral component in legacy posterior stabilised-flex total knee replacement", The Journal of Bone and Joint Surgery, vol. 89-B, No. 11, Nov. 2007, pp. 1457-1461.

(Continued)

*Primary Examiner* — David Isabella
*Assistant Examiner* — Marcia Hoffman
(74) *Attorney, Agent, or Firm* — Andrus, Sceales, Starke & Sawall, LLP

(57) ABSTRACT

The invention presents a total knee arthroplasty endoprosthesis having: a) a femoral component with a lower-radius lateral condyle, a larger-radius medial condyle and between them, a third condyle located posteriorly, superiorly and nearest the medial side, b) a tibial component with a central protruding spigot for the rotating polyethylene insert, and c) a rotating polyethylene insert, with three cavities for articulation of the femoral condyles. For initial and moderate flexion the joint functions with load bearing onto the lateral and medial articular cavities, and in advanced and final flexion with load bearing on the third articular cavity. The advantages of this endoprosthesis are enhanced maximum flexion, improved femoral axis alignment, significant posterior stabilization, favourable accommodation of tibial rotation with consequent relief of materials and fixations, and preservation of more articular fluid for lubrication and reduction of polyethylene wear.

3 Claims, 6 Drawing Sheets

FOREIGN PATENT DOCUMENTS

| | | | |
|---|---|---|---|
| EP | 0 294 298 A1 | | 12/1988 |
| FR | 2 668 703 A3 | | 5/1992 |
| GB | 2 061 730 A | | 5/1981 |
| JP | 2005-205888 | * | 7/2005 |
| WO | 98/25550 A1 | | 6/1998 |

OTHER PUBLICATIONS

G. Dendrinos et al, "The Rotaglide Knee Replacement: Evolution, Biomechanical Rationale and Results of the First 170 Cases", Proceedings from the Nordic Orthopaedic Congress, Malmo, Jun. 1992.

Athanasios C. Tsakonas et al, "Reduction of polyethylene in a congruent meniscal knee prosthesis", Acta Orthop Scand (Suppl 275) 1997; 68: pp. 127-131.

C. J. Wilson et al, "Five year review of the Rotaglide total knee Arthroplasty", The Knee 10 (2003), pp. 167-171.

A. J. Polyzoides, MD, FRCS et al, "The Rotaglide Total Knee Arthroplasty Prosthesis Design and Early Results", The Journal of Arthroplasty, vol. 11, No. 4, 1996, pp. 453-459.

A. J. Polyzoides, MD, FRCS et al, "The Rotating Knee Prostheses", Editions Scientifiques et Medicales Elsevier SAS, Surgical Techniques in Orthopaedics and Traumatology, 55-560-B-10, 2001, pp. 1-4.

Drawing page for Proposed Revision Implant, dated Nov. 30, 1984.

International Search Report for parent PCT Application No. PCT/GR2007/000018, having a mailing date of Jul. 3, 2007.

Brochure page for The Rotaglide Total Knee System—Developed in association with Mr. A.J. Polyzoides, FRCS and Dr. A. Tsakonas, MD; 1979.

Brochure pages for The Gliding Meniscal Knee—A major development in cruciate-retaining arthroplasty, 1989.

Drawing pages for Figs. I-III for Zimmer-Deloro Surgical Ltd., 1986.

Zimmer® NexGen LPS-Flex Mobile and LPS-Mobile Bearing Knees, http://www.zimmer.com/z/ctl/op/global/action/1/ id/10045/ template/MP/prcat/M3/prod/y; 1989.

Mamdouh Morgan et al, "Total Knee Arthroplasty in Young Active Patients Using a Highly Congruent Fully Mobile Prosthesis", The Journal of Arthroplasty, vol. 22, No. 4, 2007, pp. 525-530.

Masao Akagi et al, "The Bisurface Total Knee Replacement: A Unique Design for Flexion: Four-to-Nine-Year Follw-up Study", The Journal of Bone and Joint Surgery, vol. 82-A, No. 11, Nov. 2000, pp. 1626-1633.

Scott Banks et al, "Knee Motions During Maximum Flexion in Fixed and Mobile-Bearing Arthroplasties", Clinical Orthopaedics and Related Research, No. 410, May 2003, pp. 131-138.

J. Bellemans el al, "Fluoroscopic Analysis of the Kinematics of Deep Flexion in Total Knee Arthroplasty", The Journal of Bone and Joint Surgery, vol. 84-B, No. 1, Jan. 2002, pp. 50-53.

Thomas P. Andriacchi et al, "The Use of Functional Analysis in Evaluating Knee Kinematics", Clinical Orthopaedics and Related Research, No. 410, May 2003, pp. 44-53.

M.A.R. Freeman et al, "The Movement of the Normal Tibio-Femoral Joint", Journal of Biomechanics 38 (2005), pp. 197-208.

Donald G. Eckhoff et al, "Three-Dimensional Mechanics, Kinematics, and Morphology of the Knee Viewed in Virtual Reality", The Journal of Bone and Joint Surgery, vol. 87-A, Supplement 2, 2005, pp. 71-80.

Zimmer® NexGen LPS-Flex Mobile and LPS-Mobile Bearing Knees, http://www.zimmer.com/z/ctl/op/global/action/1/ id/10045/ template/MP/prcat/M3/prod/y.

* cited by examiner

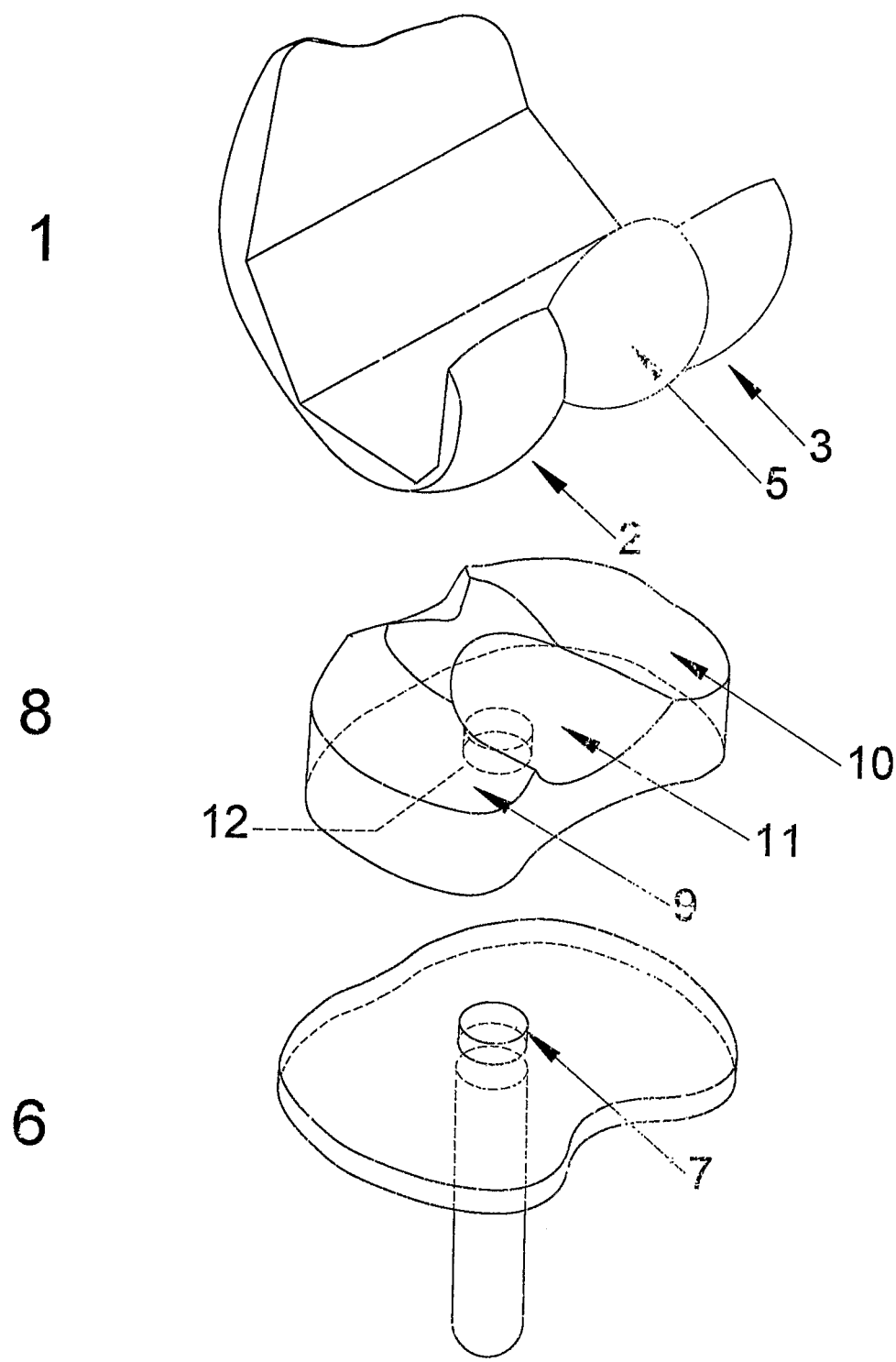
Drawing 1

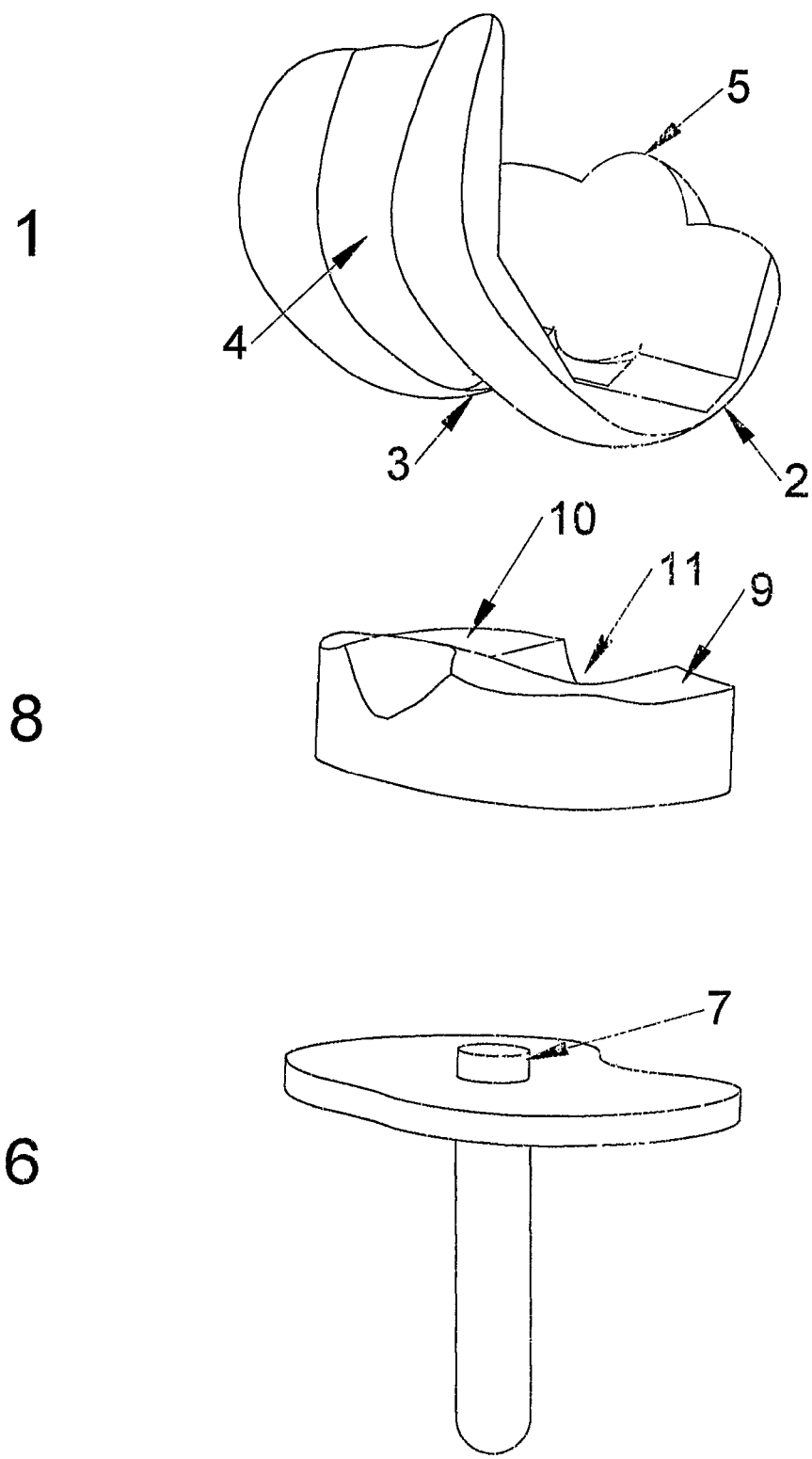
Drawing 2

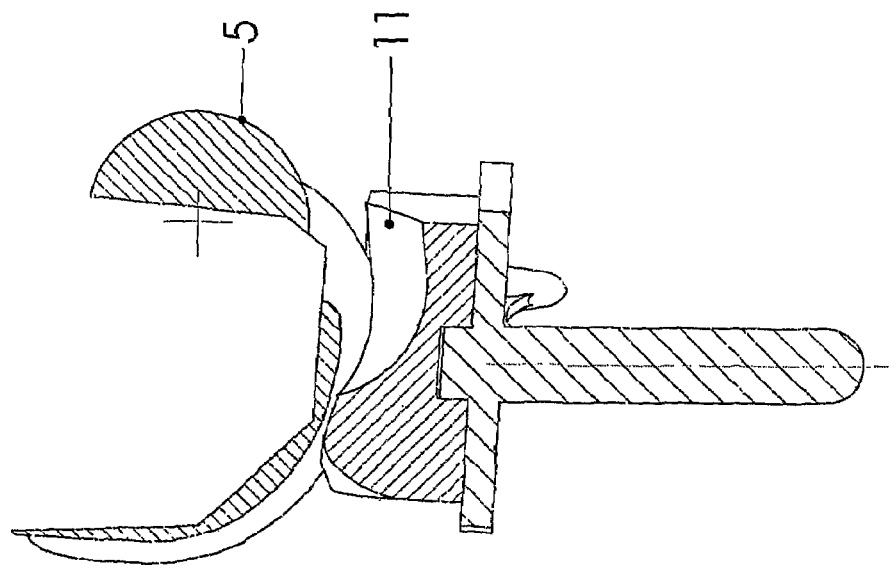
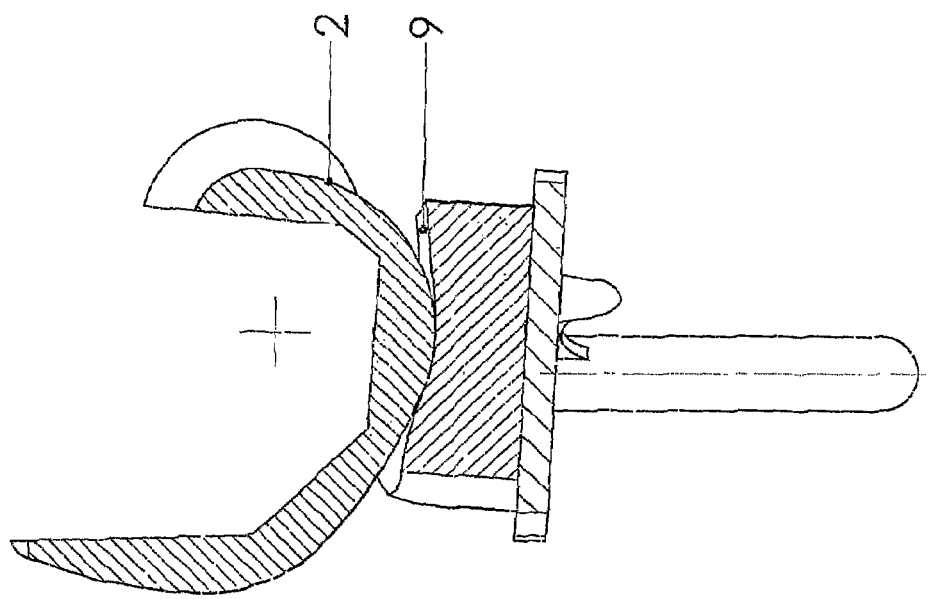
Drawing 3

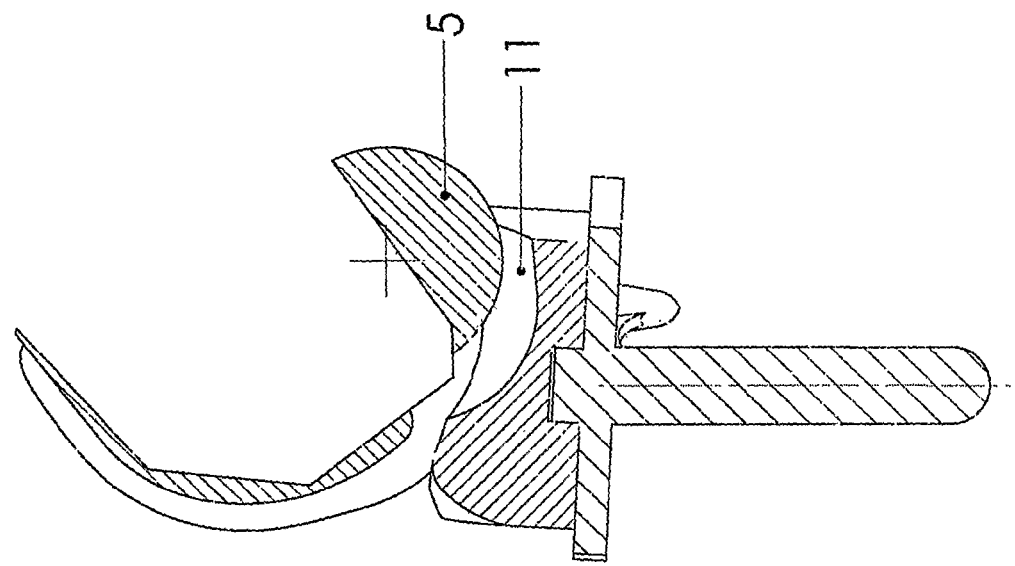
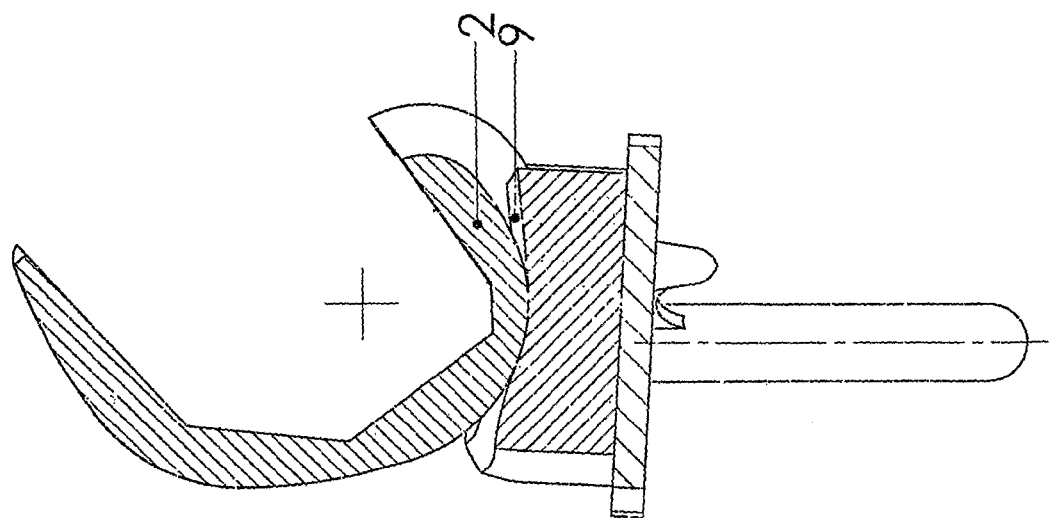
Drawing 4

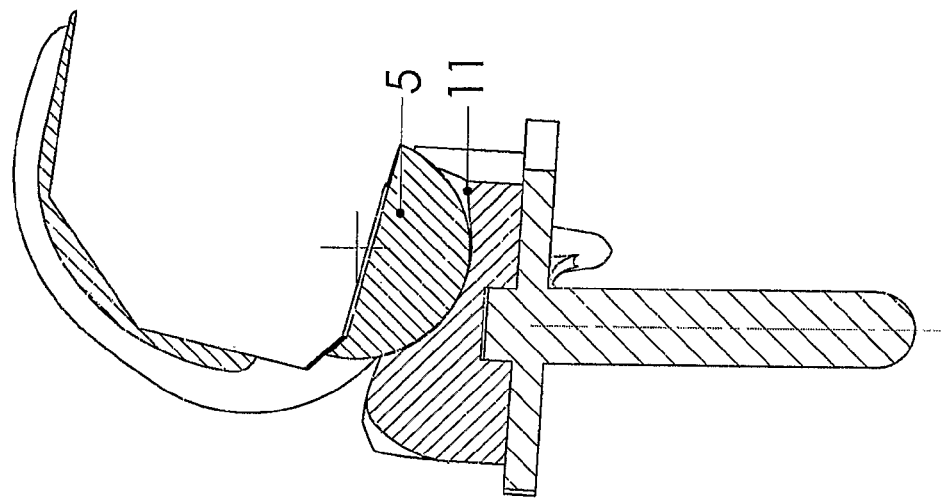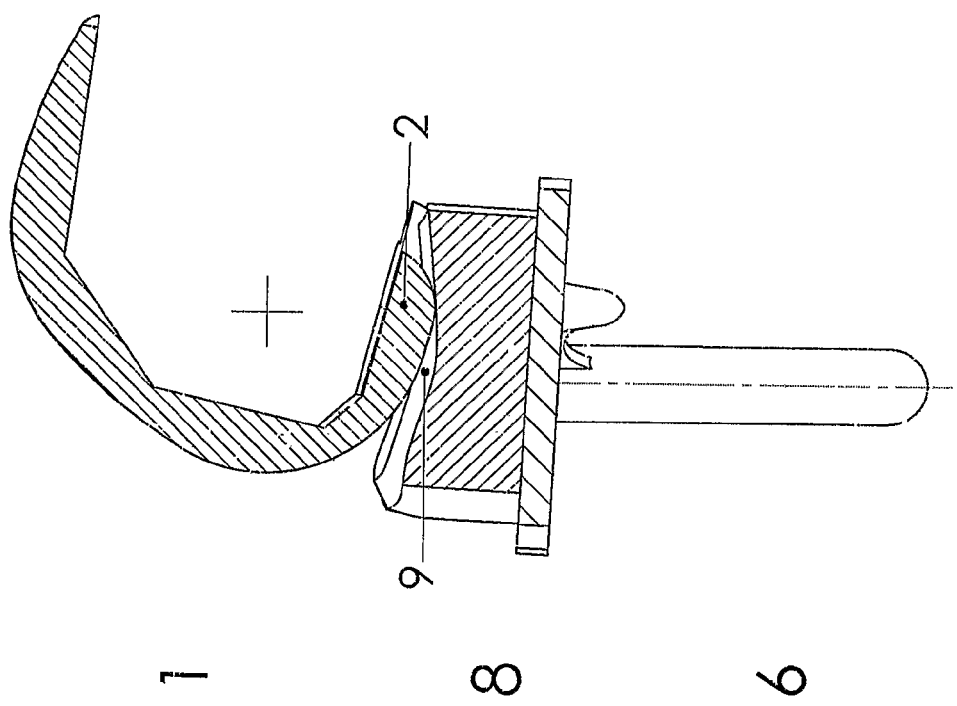
Drawing 5

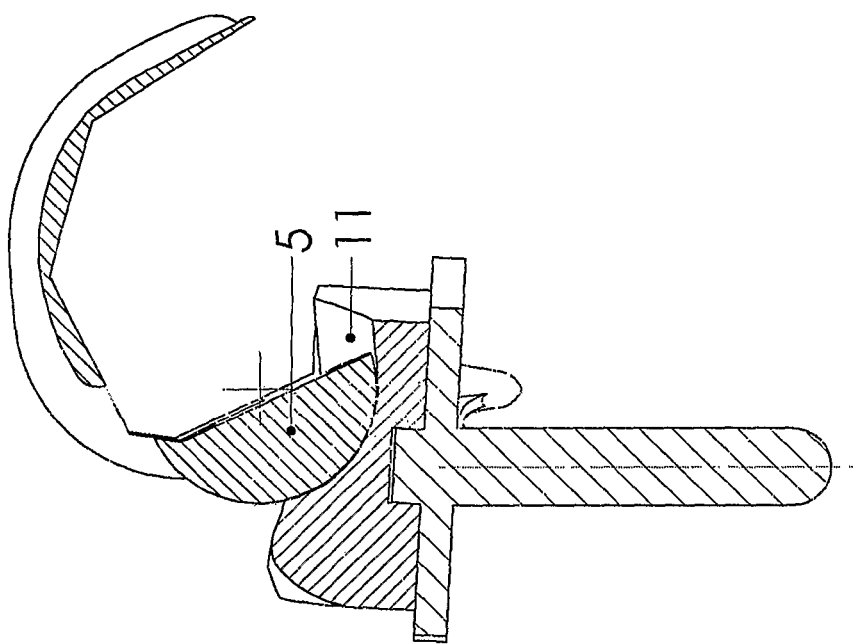
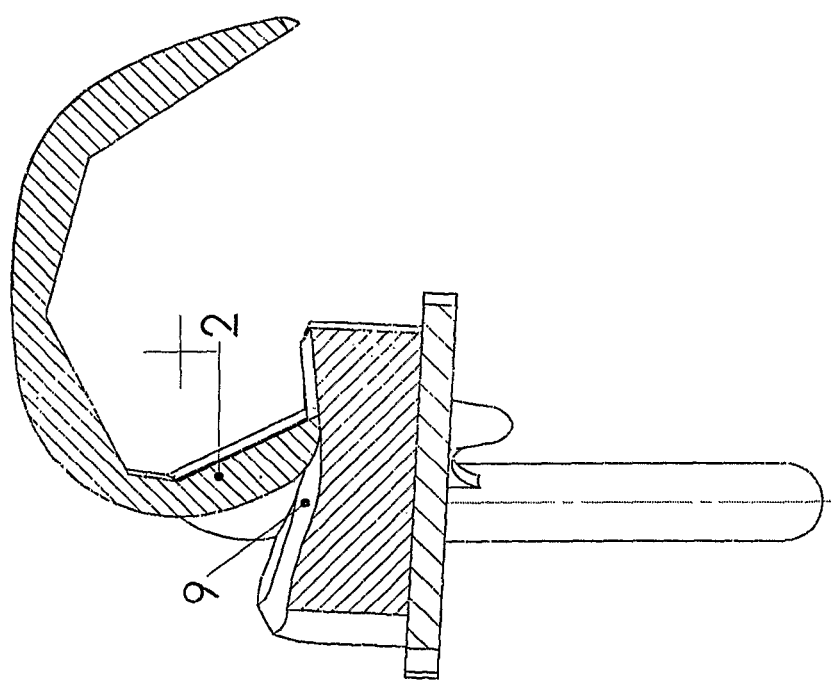
Drawing 6

TOTAL KNEE ARTHROPLASTY ENDOPROSTHESIS WITH THIRD CONDYLE AND ROTATING POLYETHYLENE INSERT

CROSS-REFERENCE TO RELATED APPLICATIONS

This application is the U.S. national stage application of International Application No. PCT/GR2007/000018, filed Mar. 16, 2007, which International Application was published on Oct. 18, 2007, as International Publication No. WO 2007/116232 A1 in the English language. The International Application claims priority of Greek Patent Application No. 20060100216, filed Apr. 7, 2006.

BACKGROUND OF THE INVENTION

The invention described herein is an endoprosthesis for total knee arthroplasty (TKA), the surgical technique meant to reconstruct and rehabilitate the painful and deformed knee joint.

The motion of the normal knee joint is a continuous combination of rolling, sliding and rotation, valgus-varus angular displacement of the femoral condyles on the tibial articular surface and the menisci, which collectively is referred to as flexion-extension. These complex motion components take place in three dimensions and always in a varying combination, and are controlled by the shape of the articular surfaces, the articular capsule, the menisci and the ligaments.

Longterm and good quality function of a TKA endoprosthesis is influenced by and depends upon the manner adopted by the implant design to solve the following interrelated problems: the wear of materials, the fixation of the endoprosthesis and the satisfactory joint motion.

The femoral component of a TKA endoprosthesis resembles the distal part of the human femur and is either metallic or ceramic. The tibial component of a TKA endoprosthesis is metallic, having a flat upper surface and possessing at least one stem on the lower surface for fixation onto the tibial bone. Between the femoral and tibial components another one is inserted: the polyethylene insert, which may be either fixed or mobile on the flat upper surface of the tibial component.

When the polyethylene insert is mobile, its motion is controlled by spigots protruding from the upper surface of the tibial component and corresponding recesses on the lower surface of the polyethylene insert, or vice versa. This control system may allow rotation or also simultaneously anteroposterior translation.

During TKA surgery, the articular cartilage and the subchondral bone are removed from the distal femur and the proximal tibia. Using appropriate instrumentation, these anatomical areas are contoured in order to allow the exact fitting of the endoprosthetic components, with or without use of acrylic resin cement. The anterior cruciate ligament is most of the times removed, while the posterior cruciate ligament is either preserved or sacrificed and substituted by functional characteristics of the implants. Special surgical attention is being paid in the preservation of the collateral ligaments of the knee and the symmetry of the ligamentous tensions developed during joint motion.

From the above description, it can be appreciated that with a given competent surgical technique, the longterm good quality function of a TKA endoprosthesis lies with the correct design of its individual components; this latter condition being perceived in a particular biomechanical sense reflecting the kinematic compatibility between the pre-existing musculoskeletal flexion-extension mechanism of the patient and the corresponding mechanism to which the individual components obey by-design.

Successive design generations attempted to fulfil the above condition, initially using fixed polyethylene inserts and later on mobile ones; the latter introduced in order to better address the issue of material wear and longevity. Mobile polyethylene inserts in particular, were introduced based on the rationale that, while the endoprosthesis should have the required congruent articular surfaces within the full range of joint motion and independently from the tibial rotation with respect to the femur, on the other hand it (the endoprosthesis) should direct a large amount of the developed loading towards the surrounding soft tissues (capsule, ligaments, tendons-muscles), thus protecting the polyethylene as well as the fixation of the implants onto the bones.

Today, when correctly implanted, all commercially available TKA endoprostheses generally demonstrate good clinical results, with a survival percentage of 95% at ten years from surgery.

However, all commercially available TKA endoprostheses present today the following disadvantages:

a) They demonstrate limited maximum flexion angle (ranging between 115 to 127 degrees), which is not compatible with activities of younger patients as well as with daily activities of populations needing to flex their knee joints above 150 degrees, and b) When driven to higher knee flexion angles, they present an extremely reduced area of load bearing articular surface between polyethylene and femoral condyles, which results in faster material wear and loss of implants fixation onto the bones.

SUMMARY OF THE INVENTION

The invention described herein is an endoprosthesis for total knee arthroplasty (TKA), with which the above disadvantages are addressed and which consists of: a metallic femoral component, a metallic tibial component and a mobile polyethylene insert.

BRIEF DESCRIPTION OF THE DRAWINGS

Drawing FIG. 1 is a posterior isometric view of a TKA endoprosthesis for a left knee joint.

Drawing FIG. 2 is an anterior isometric view of the TKA endoprosthesis for a left knee joint.

Drawing FIG. 3 depicts a joint at the initial full extension.

Drawing FIG. 4 depicts the joint at a stage representative of initial and moderate flexion.

Drawing FIG. 5 depicts the joint at a stage representative of rather advanced flexion.

Drawing FIG. 6 depicts the joint at a stage representative of final flexion.

DETAILED DESCRIPTION OF THE DRAWINGS

The posterior and anterior isometric views of the invented TKA endoprosthesis are exhibited in drawings 1 and 2 respectively, for a left knee joint:

The femoral component (1) of the endoprosthesis possesses two asymmetric femoral condyles which are sections of spheres: the lateral condyle (2) with a smaller radius and the medial condyle (3) with a larger radius. Between these two condyles, the femoral component possesses a third spherical or elliptical condyle (5), which with respect to the other two is located more posteriorly, superiorly and nearest the medial condyle (i.e. located towards the medial side). For the purpose of patella sliding and adequate function of the extension mechanism, the anterior aspect of the femoral component possesses a concave groove (4) running along a direction from proximally-lateral to distally-medial, and which gradually from proximally to distally becomes broader and shallower.

The tibial component (6) possesses a flat upper surface and a protruding rotation spigot (7) located at its centre. On the lower surface of the tibial component there is a system of stems for fixation on the tibial bone.

The polyethylene insert (8) follows the morphology of the three condyles of the femoral component (1), in order to serve their articulation during the various stages throughout the full flexion range of the knee joint. For the articulation of the asymmetric lateral (2) and medial (3) femoral condyles, on its upper surface this component possesses two respectively asymmetric but equally deep cavities, one laterally (9) and one medially (10). Furthermore, for the articulation of the third femoral condyle (5), this component possesses the central cavity (11) which, due to its location, engages the condyle (5) at an advanced and final stage of flexion, when this condyle besides acting as an axis of flexion and rotation, also acts as a posterior stabilizer.

In the centre of its lower surface, the polyethylene insert (8) has an appropriate bore (12) in order to be fitted on the rotation spigot (7) which lies on the tibial component (6). The imaginary axis of rotation for the polyethylene insert lies therefore on the mid-sagittal plane of the endoprosthesis and consequently laterally to the third condyle (5).

Drawings 3, 4, 5 and 6 describe the function of the invented TKA endoprosthesis, showing sagittal sections on the lateral condyle (2) and of the third condyle (5), for the various stages of flexion:

Drawing 3 describes the joint at the initial full extension (i.e. zero degrees of flexion).

Drawing 4 describes the joint at a stage representative of initial and moderate flexion (i.e. a flexion range including the angle of 40 degrees encountered during the stance phase of gait, the angle of 70 degrees encountered during the swing phase of gait and until approximately 100 degrees).

Drawing 5 describes the joint at a stage representative of rather advanced flexion (i.e. a flexion range above 100 degrees).

Drawing 6 describes the joint at a stage representative of final flexion (i.e. a flexion range up to 160 degrees, for various other activities beyond gait).

After TKA surgery and with the patient finally in an active load bearing postoperative condition, the invented endoprosthesis will function according to two fundamental ways, as follows:

a) From full extension (drawing 3) and for initial and moderate flexion (drawing 4), the function is based on the articulation between the congruent load-bearing articular surfaces of the polyethylene insert and the corresponding surfaces of the femoral condyles, that is between the cavities (9) and (10) on one hand and the lateral (2) and medial (3) femoral condyles on the other.

b) In advanced flexion (drawing 5) and subsequently in final flexion (drawing 6), the function is mainly based on the articulation between the congruent load-bearing central cavity (11) of the polyethylene insert and the third femoral condyle (5) and much less on the articulation between the polyethylene insert and lateral and medial femoral condyles, which at this stage play a continuously inferior role.

During the above functional configurations and besides the significantly increased range of maximum flexion, the function of the invented TKA endoprosthesis demonstrates the following additional advantages:

a) At any stage throughout the whole flexion range, the asymmetrical femoral condyles, namely the lower radius lateral condyle (2) and the larger radius medial condyle (3), impose between the anatomical femoral and tibial axes a geometrical relationship which approaches the physiological valgus of the knee joint.

b) At any stage during advanced and final flexion range, the third condyle (5), besides acting as a rotation axis for the joint, it also acts, due to its superior-posterior position, as a posterior stabilizer; thus maintaining the femoral component in a appropriately posterior relationship with respect to the polyethylene insert (8) and consequently with respect to the tibial component (6). This is fact actually favours completion of full flexion without material impingement.

c) At any stage during advanced and final flexion range, the third condyle (5), due to its location nearest to the medial condyle (i.e. towards the medial side), not only has an enhanced contribution in load bearing, but also encourages during flexion the rotation of the tibia about the axis (7), which is located more laterally.

d) The rotating polyethylene insert (8) taking advantage of its mobility about the rotation axis (7) on the tibial component (6), is enabled to accommodate the needs of the joint in external or internal rotation; thus removing such wearing burden from the articular surfaces and relieving implant fixation sites, even in very high flexion angles where the tibia may need to internally rotate as much as 20 degrees.

e) The congruency of all articular bearing surfaces between polyethylene and condyles ensures preservation of more articular fluid between them, thus enhancing lubrication and contributing to the reduction of material wear.

The invented TKA endoprosthesis reported herein addresses the disadvantages demonstrated by the commercially available TKA endoprostheses, as it fulfils the biomechanical prerequisites which are necessary for an unconstrained full flexion of the joint with simultaneous protection of the polyethylene insert from loads born by articular surfaces of limited area. These characteristics have a beneficial effect in ensuring adequate joint functionality even in very high flexion angles and in protecting the polyethylene, which to a large extent defines the biological and mechanical stability and longevity of the arthroplasty.

The invention claimed is:

1. A total knee arthroplasty endoprosthesis comprising:
a metallic femoral component including a spherical lateral condyle surface and a spherical medial condyle surface, the lateral condyle surface having a smaller radius than the medial condyle surface;
a third condyle located between, posterior, and superior the medial condyle surface and the lateral condyle surface, and offset on the metallic femoral component in a direction of the medial condyle surface;
a metallic tibial component including a central spigot; and
a polyethylene insert including a bore that engages the central spigot, the polyethylene insert being rotatable about the central spigot of the metallic tibial component, the polyethylene insert having a medial cavity in conformity with a shape of the medial condyle surface and a lateral cavity in conformity with a shape of the lateral condyle surface, wherein the medial and lateral cavities are asymmetrical but equally deep, the polyethylene insert further comprises a third cavity in conformity with a shape of the third condyle, and located between, inferior, and posterior the medial cavity and the lateral cavity, and offset on the polyethylene insert in a direction of the medial cavity;

wherein the medial and lateral condyle surfaces respectively engage the medial and lateral cavities at a medial bearing surface and a lateral bearing surface such as to be adapted to impose a geometrical relationship between an anatomic femoral axis and an anatomic tibial axis that approaches a physiological valgus of a knee joint;

wherein at an advanced stage of flexion between the femoral component and the tibial component, the third condyle engages the third cavity at a central bearing surface that replaces the medial bearing surface and the lateral bearing surface, the central bearing surface being larger than either of the medial or lateral bearing surfaces;

wherein the offset of the third condyle towards the medial condyle, assists rotation of the polyethylene insert with respect to the metallic tibial component about an axis defined by the bore and central spigot;

wherein the central spigot of the metallic tibial component and the bore of the polyethylene insert are aliened on a mid-sagital plane of the total knee arthroplasty endoprosthesis wherein the third condyle is medially offset from the axis defined by the bore and central spigot, wherein the engagement of the central spigot with the bore prevents translational movement of the polyethylene insert, while permitting only rotational movement of the polyethylene insert about the axis defined by the bore and central spigot.

2. The total knee arthroplasty endoprosthesis of claim 1, wherein the third condyle is spherical.

3. The total knee arthroplasty endoprosthesis of claim 1 wherein the third condyle is ellipsoidical.

* * * * *